United States Patent
Ehmke et al.

(10) Patent No.: US 10,117,685 B2
(45) Date of Patent: Nov. 6, 2018

(54) BONE FIXATION WITH A PIN AND A COLLAR

(71) Applicant: Acumed LLC, Hillsboro, OR (US)

(72) Inventors: Larry W. Ehmke, Beaverton, OR (US); Brian R. Conley, Portland, OR (US)

(73) Assignee: Acumed LLC, Hillsboro, OR (US)

( * ) Notice: Subject to any disclaimer, the term of this patent is extended or adjusted under 35 U.S.C. 154(b) by 372 days.

(21) Appl. No.: 14/746,722

(22) Filed: Jun. 22, 2015

(65) Prior Publication Data

US 2015/0374411 A1 Dec. 31, 2015

Related U.S. Application Data

(60) Provisional application No. 62/016,883, filed on Jun. 25, 2014.

(51) Int. Cl.
*A61B 17/72* (2006.01)
*A61B 17/68* (2006.01)
*A61B 17/00* (2006.01)

(52) U.S. Cl.
CPC ........ *A61B 17/7233* (2013.01); *A61B 17/686* (2013.01); *A61B 17/7208* (2013.01); *A61B 2017/00004* (2013.01)

(58) Field of Classification Search
CPC .............. A61B 17/7233; A61B 17/683; A61B 17/7008; A61B 17/7019–17/702;
(Continued)

(56) References Cited

U.S. PATENT DOCUMENTS

| | | |
|---|---|---|
| 2,952,254 A | 9/1960 | Keating |
| 3,351,054 A | 11/1967 | Florek |

(Continued)

FOREIGN PATENT DOCUMENTS

| | | |
|---|---|---|
| EP | 1195142 A2 | 4/2002 |
| EP | 1348380 A1 | 10/2003 |

(Continued)

OTHER PUBLICATIONS

Dogra et al., "Dia-metaphyseal distal tibial fractures—treatment with a shortened intramedullary nail; A review of 15 cases", Injury, International Journal of the Care of the Injured, vol. 31, 2000, pp. 799-804.

(Continued)

*Primary Examiner* — Marcia Watkins
(74) *Attorney, Agent, or Firm* — Kolisch Hartwell, P.C.

(57) ABSTRACT

System, including methods and devices, for bone fixation with a pin and a collar. In exemplary embodiments, the system may comprise a pin configured to be inserted into a bone, and a deformable collar to retain the pin in the bone. The collar may be configured to be operatively disposed on the pin such that the collar extends more than halfway and less than completely around the pin. The pin and the collar may have complementary surface features that discourage sliding of the collar along a long axis of the pin. In some embodiments, the collar may be configured to be operatively disposed on the pin at a plurality of discrete, alternative axial positions along the long axis of the pin. The pin may be cut to a desired length.

16 Claims, 10 Drawing Sheets

(58) Field of Classification Search
CPC ........ A61B 17/7049; A61B 17/7041–17/7275;
A61B 17/744; A61B 17/7258
See application file for complete search history.

(56) References Cited

U.S. PATENT DOCUMENTS

| | | | |
|---|---|---|---|
| 4,013,071 A | | 3/1977 | Rosenberg |
| 4,629,463 A | * | 12/1986 | Grundei ................ A61B 17/72 606/326 |
| 4,688,561 A | | 8/1987 | Reese |
| 4,776,330 A | | 10/1988 | Chapman et al. |
| 4,793,335 A | | 12/1988 | Frey et al. |
| 5,013,314 A | | 5/1991 | Firica et al. |
| 5,203,784 A | | 4/1993 | Ross et al. |
| 6,168,595 B1 | | 1/2001 | Durham et al. |
| 6,620,195 B2 | | 9/2003 | Goble et al. |
| 7,935,138 B1 | | 5/2011 | Richelsoph |
| 8,337,537 B2 | | 12/2012 | Pelo et al. |
| 8,672,986 B2 | | 3/2014 | Klaue et al. |
| 2002/0173792 A1 | | 11/2002 | Severns et al. |
| 2005/0071005 A1 | * | 3/2005 | Carli .................... A61F 2/4455 623/17.11 |
| 2005/0216012 A1 | | 9/2005 | Willmen |
| 2006/0095040 A1 | | 5/2006 | Schlienger et al. |
| 2006/0264951 A1 | | 11/2006 | Nelson et al. |
| 2008/0269893 A1 | * | 10/2008 | Bhatnagar .......... A61B 17/7208 623/11.11 |
| 2011/0034925 A1 | | 2/2011 | Tipirneni et al. |
| 2013/0079776 A1 | | 5/2013 | Zwirkoski et al. |
| 2013/0131822 A1 | | 5/2013 | Lewis et al. |

FOREIGN PATENT DOCUMENTS

| | | |
|---|---|---|
| FR | 2699065 A1 | 6/1994 |
| WO | 2011031495 A2 | 3/2011 |
| WO | 2011037614 A1 | 3/2011 |
| WO | 2013177252 A1 | 11/2013 |

OTHER PUBLICATIONS

Thomas, Shane, Authorized Officer, U.S. Receiving Office, "International Search Report" in connection with related International Patent Application No. PCT/US2015/037026, dated Sep. 30, 2015, 3 pages.

Thomas, Shane, Authorized Officer, U.S. Receiving Office, "Written Opinion of the International Searching Authority" in connection with related International Patent Application No. PCT/US2015/037026, dated Sep. 30, 2015, 8 pages.

European Patent Office, "Extended European Search Report" in connection with related European Patent Application No. 15811106.2, dated Feb. 14, 2018, 8 pgs.

* cited by examiner

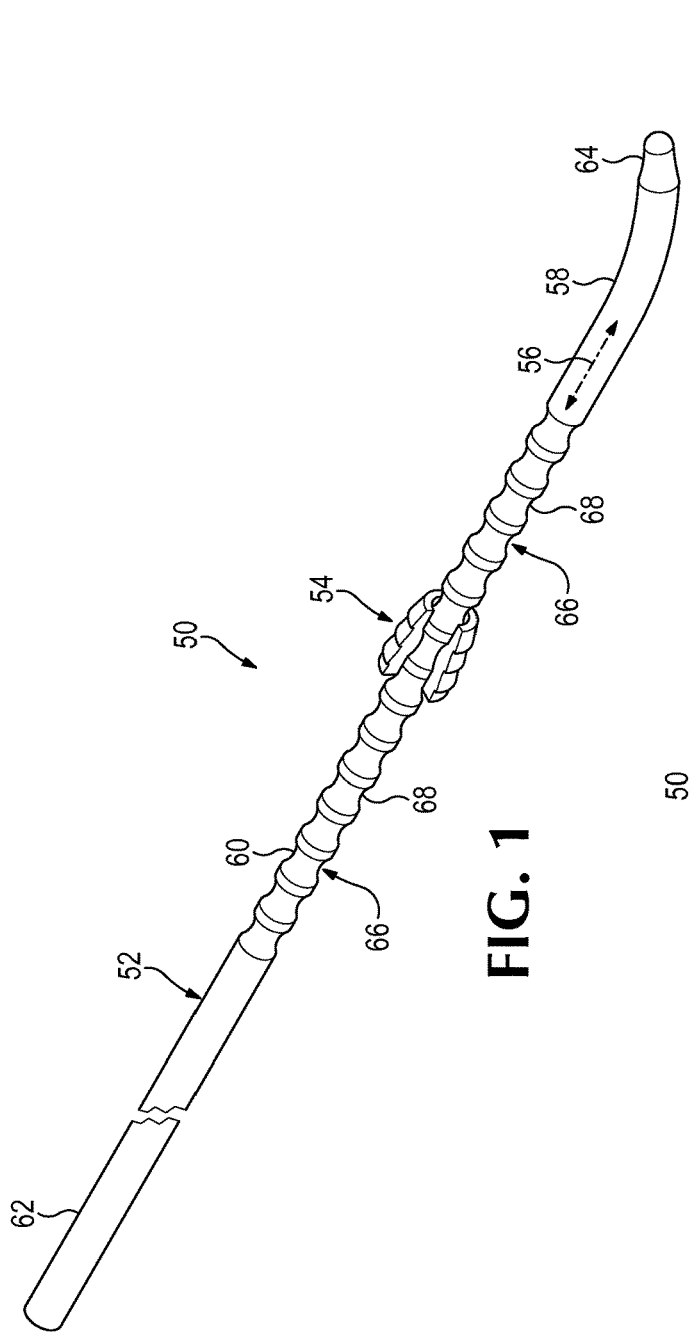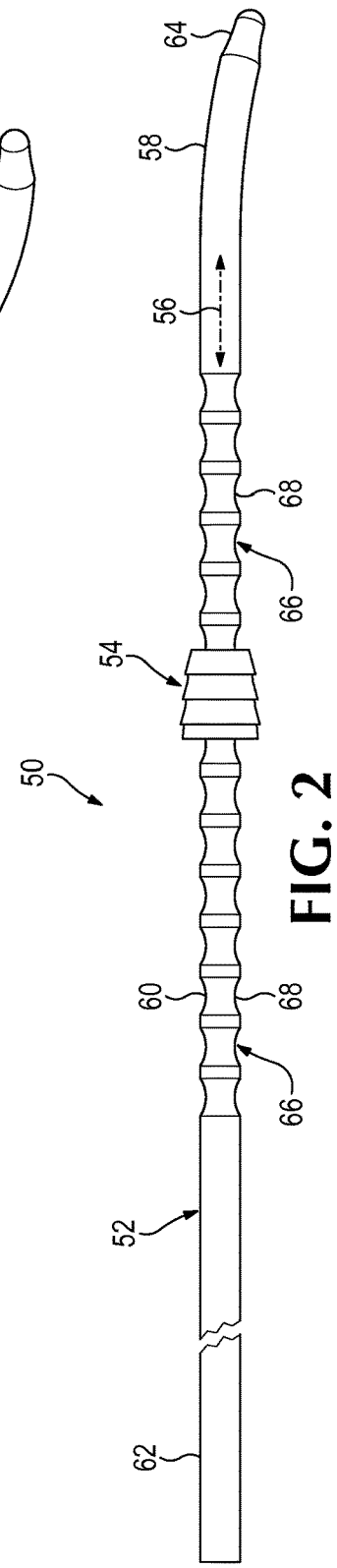

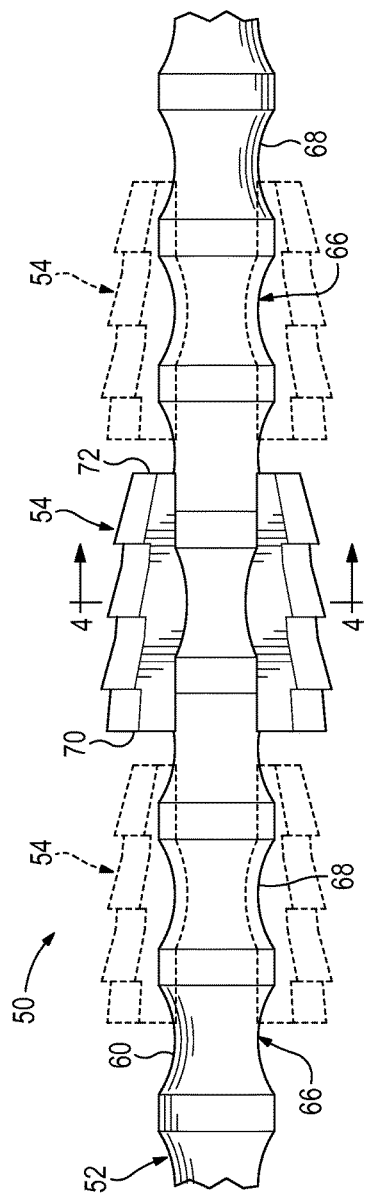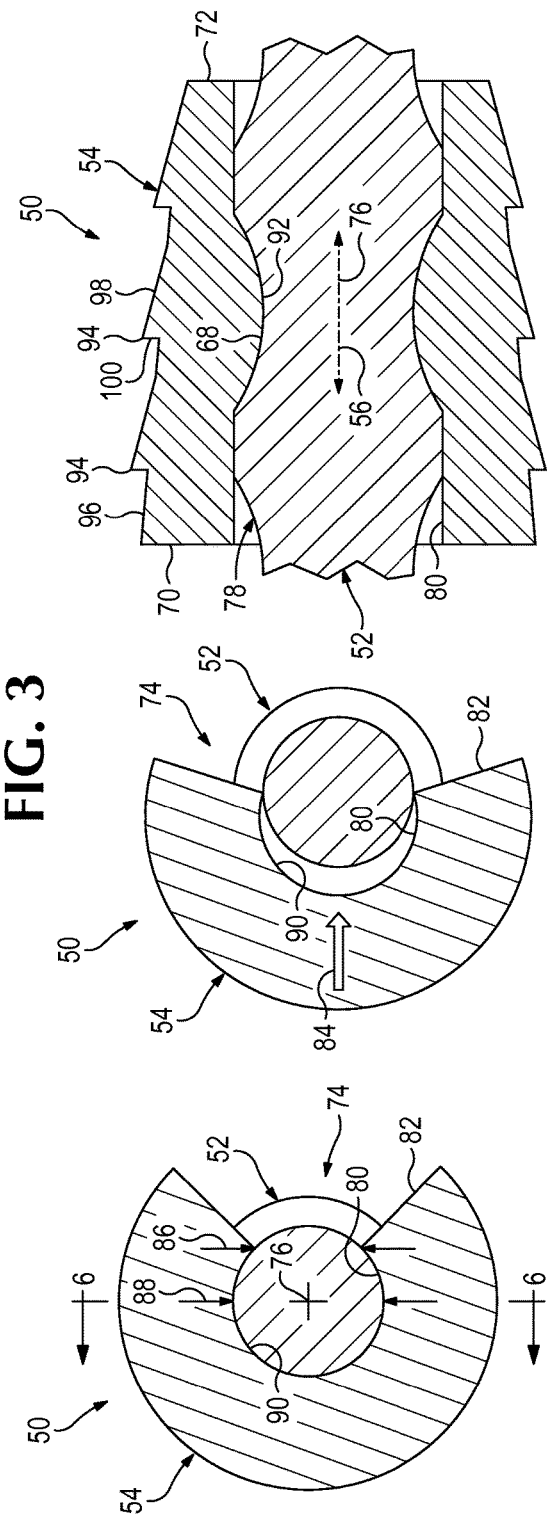

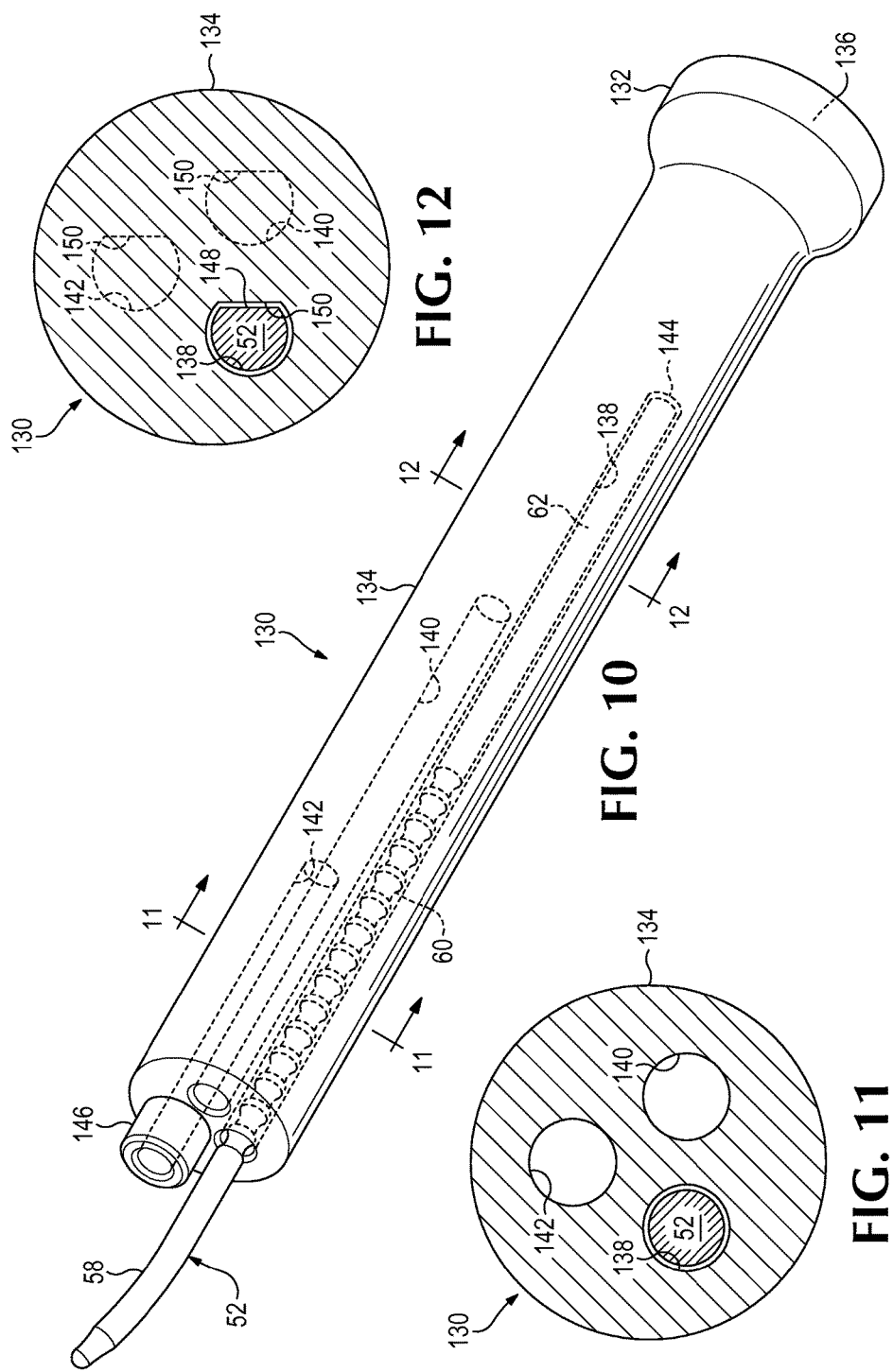

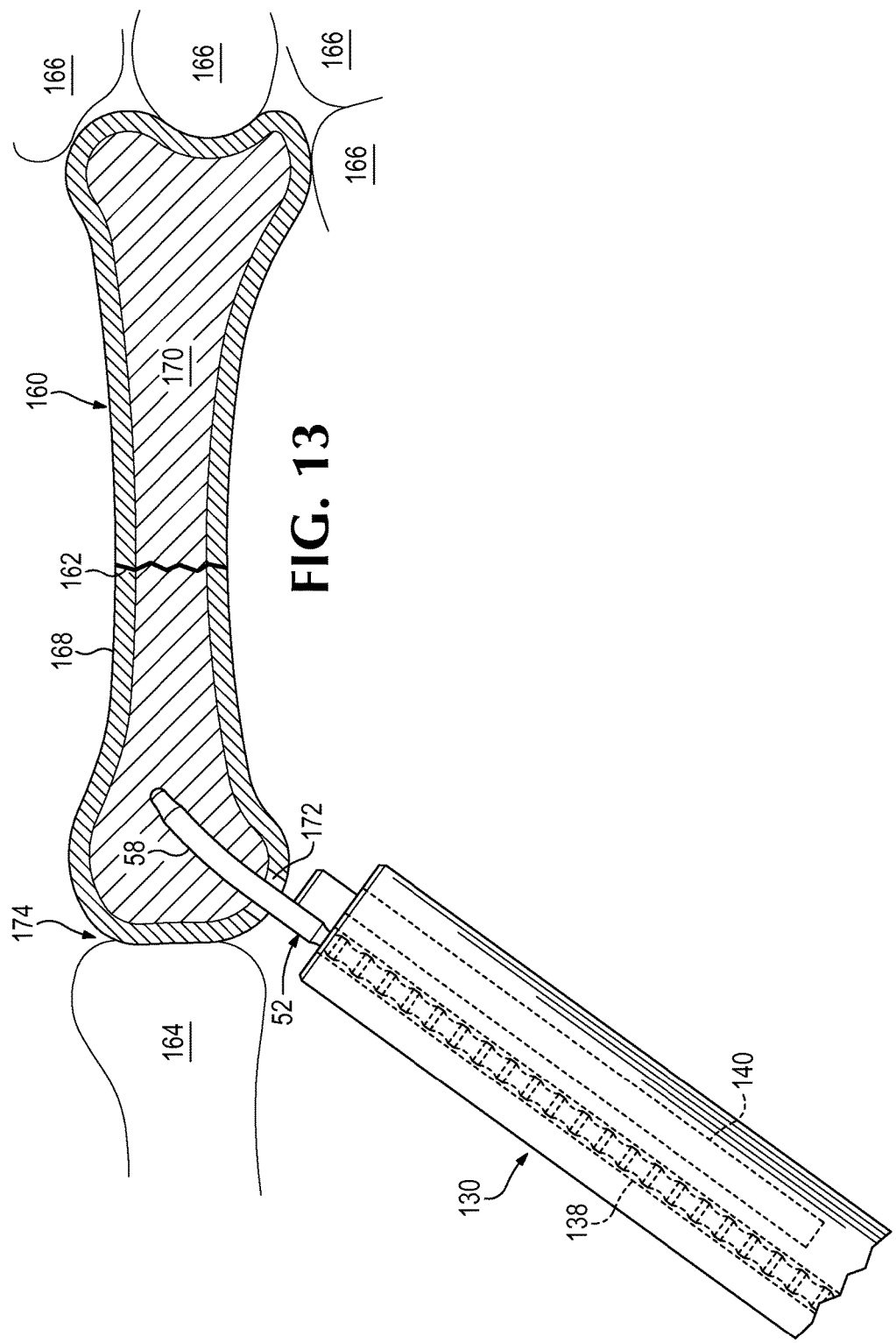

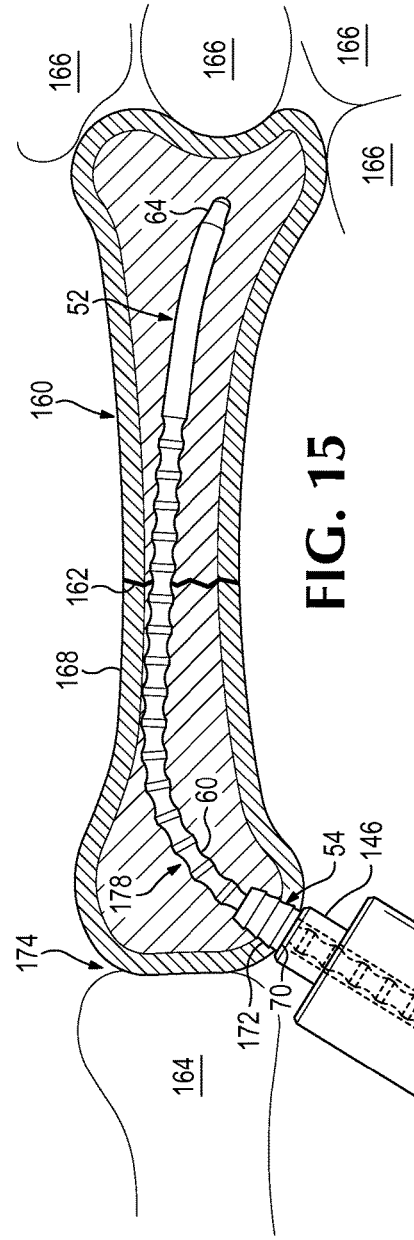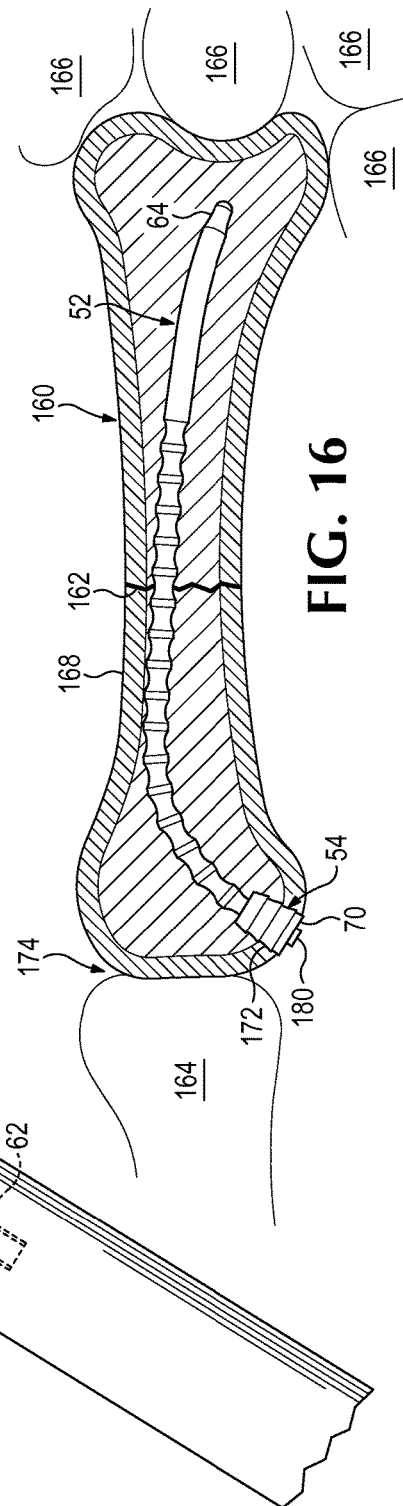

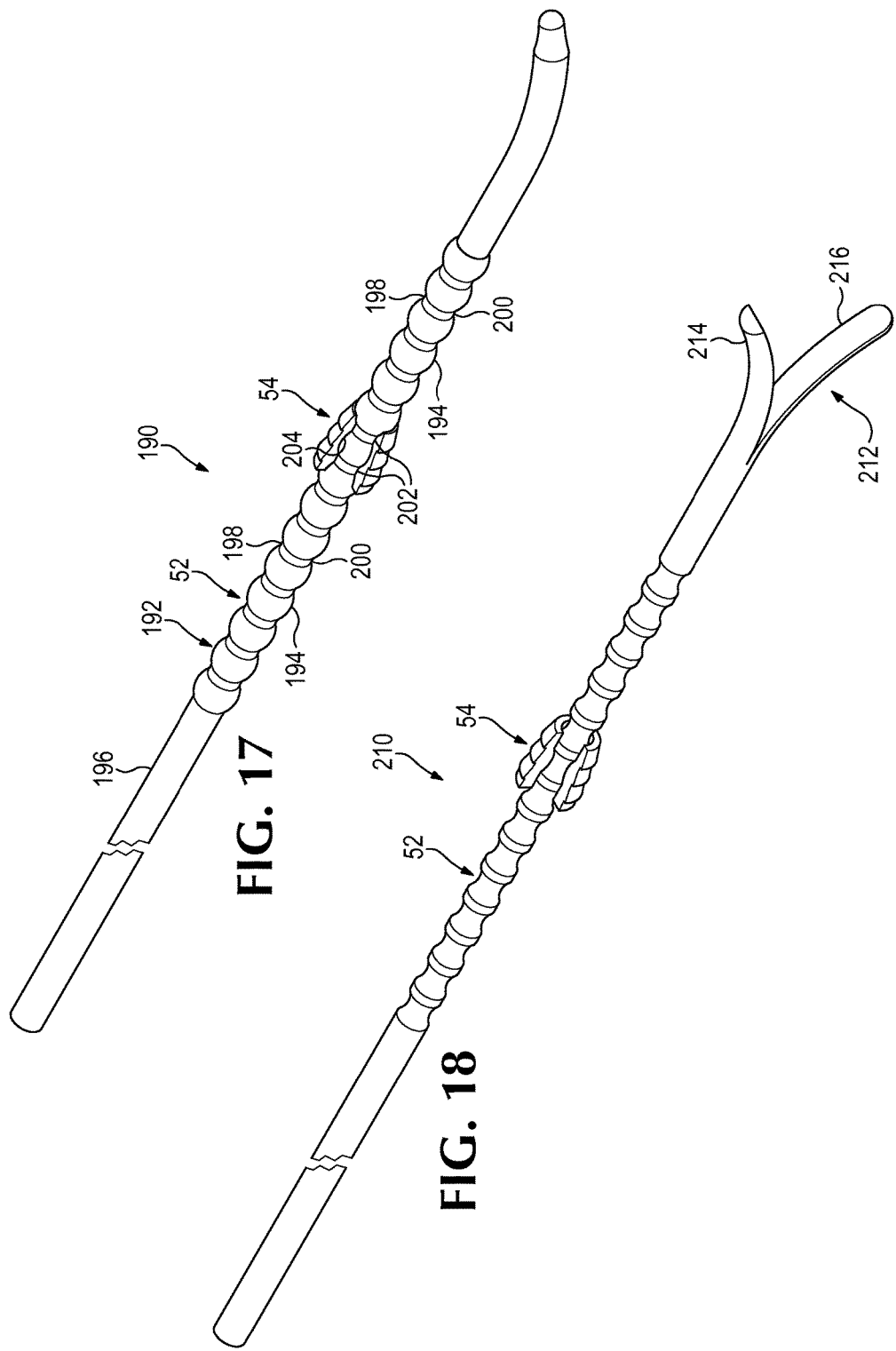

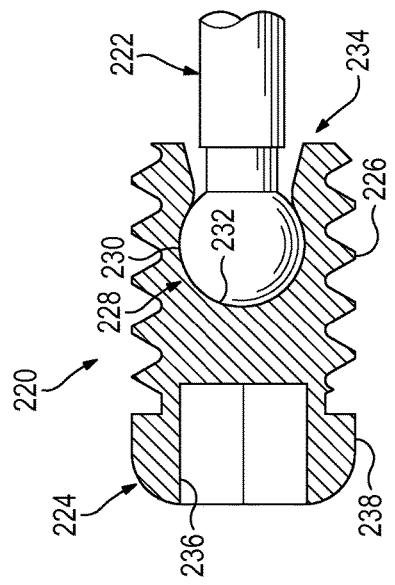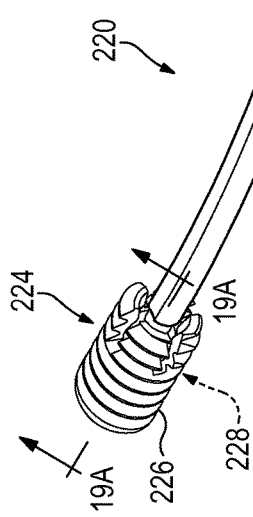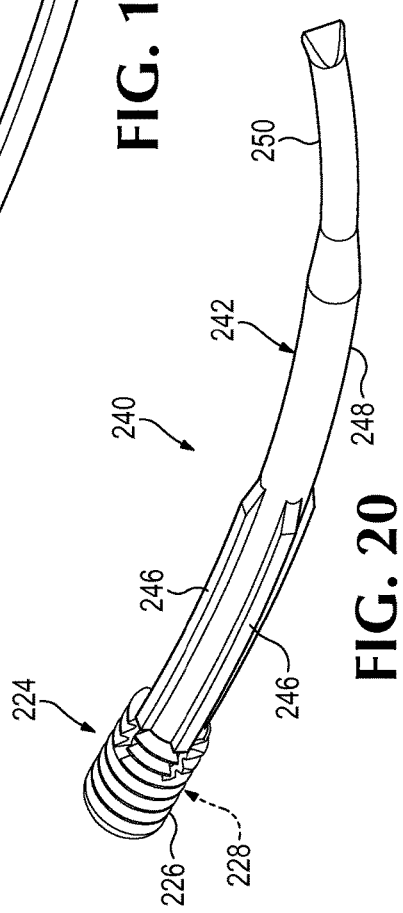

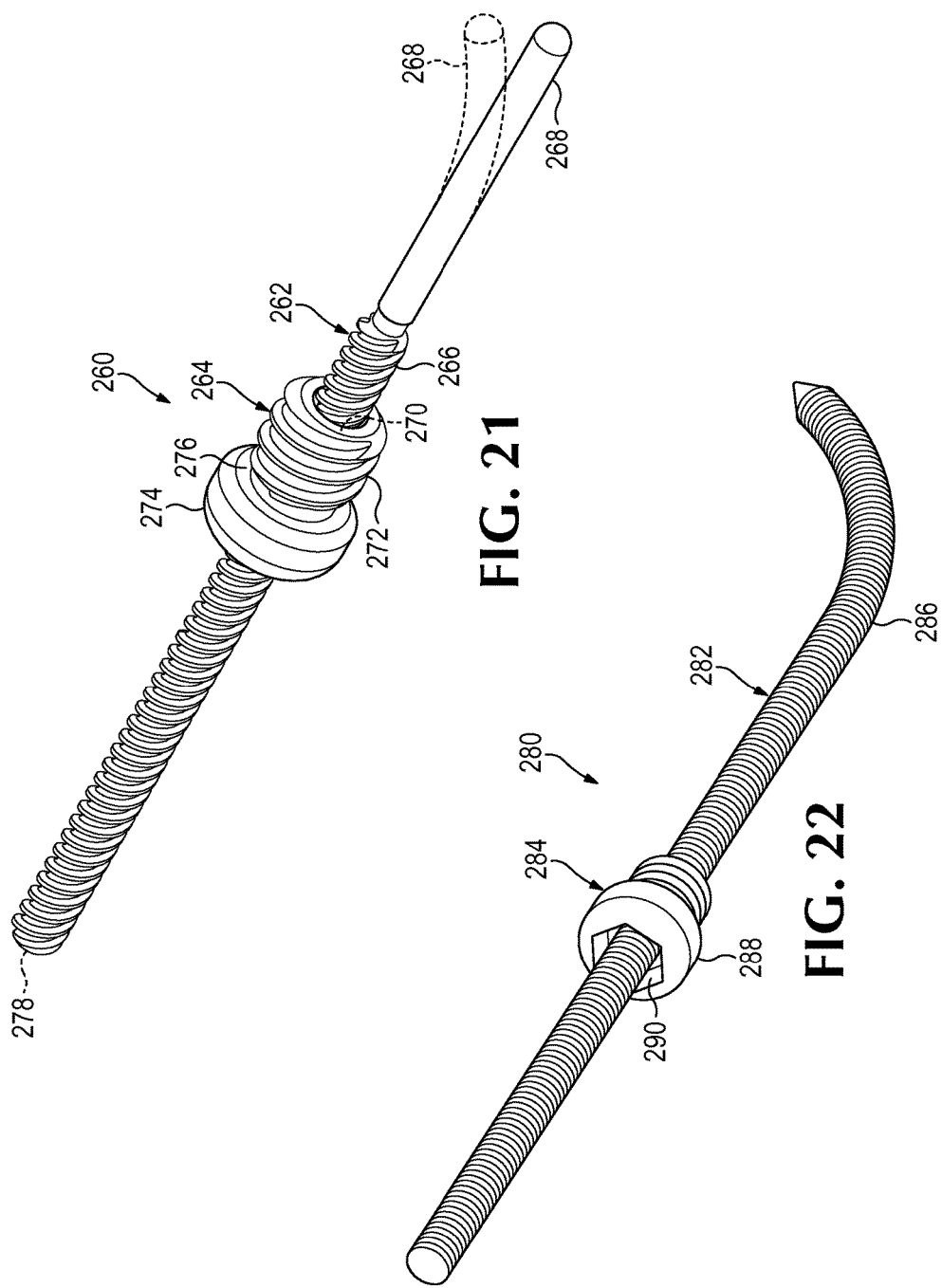

BONE FIXATION WITH A PIN AND A COLLAR

CROSS-REFERENCE TO PRIORITY APPLICATION

This application is based upon and claims the benefit under 35 U.S.C. § 119(e) of U.S. Provisional Patent Application Ser. No. 62/016,883, filed Jun. 25, 2014, which is incorporated herein by reference in its entirety for all purposes.

INTRODUCTION

The human skeleton is composed of 206 individual bones that perform a variety of important functions, including support, movement, protection, storage of minerals, and formation of blood cells. To ensure that the skeleton retains its ability to perform its important functions, and to reduce pain and disfigurement, fractured bones should be repaired promptly and properly. Typically, a fractured bone is treated using a fixation device that reinforces the fractured bone and keeps it aligned during healing. Fixation devices for internal fixation include bone plates, nails, wires, and screws.

The size, shape, and function of a bone can dictate the best approach for fixation. For example, fractured bones of the arms and legs are often stabilized with bone plates or intramedullary nails that can withstand a substantial load. However, these types of fixation devices, when scaled down, may be less suitable for the smaller long bones of the hands and feet. New fixation options are needed.

SUMMARY

The present disclosure provides a system, including methods and devices, for bone fixation with a pin and a collar. In exemplary embodiments, the system may comprise a pin configured to be inserted into a bone, and a deformable collar to retain the pin in the bone. The collar may be configured to be operatively disposed on the pin such that the collar extends more than halfway and less than completely around the pin. The pin and the collar may have complementary surface features that discourage sliding of the collar along a long axis of the pin. In some embodiments, the collar may be configured to be operatively disposed on the pin at a plurality of discrete, alternative axial positions along the long axis of the pin. The pin may be cut to a desired length.

BRIEF DESCRIPTION OF THE DRAWINGS

FIG. 1 is a view of an exemplary embodiment of a bone fixation system including a pin and a collar assembled with the pin and configured to retain the pin in bone, in accordance with aspects of the present disclosure.

FIG. 2 is a side view of the fixation system of FIG. 1.

FIG. 3 is a magnified, fragmentary view of the fixation system of FIG. 1, taken toward an opposite side of the system relative to FIG. 2, with exemplary alternative axial positions of the collar shown in phantom.

FIG. 4 is a cross-sectional view of the fixation system of FIG. 1, taken generally along line 4-4 of FIG. 3.

FIG. 5 is another cross-sectional view of the fixation system of FIG. 1, taken as in FIG. 4 except during assembly of the collar with the pin, with the collar maximally deformed by the pin.

FIG. 6 is a longitudinal sectional view of the fixation system of FIG. 1, taken generally along line 6-6 of FIG. 4.

FIG. 10 is a view of the pin of FIG. 1 operatively received in an exemplary driver for the pin, in accordance with aspects of the present disclosure.

FIG. 11 is a cross-sectional view of the pin and the driver of FIG. 10, taken generally along line 11-11 of FIG. 10 through the pin and the driver.

FIG. 12 is a cross-sectional view of another exemplary embodiment of the pin and driver of FIG. 10, taken at a position corresponding to line 12-12 of FIG. 10 through the pin and the driver and showing corresponding flats that may be formed on the pin and by a wall of each pin-receiving hole of the driver, to allow the driver to transmit torque to the pin, in accordance with aspects of the present disclosure.

FIG. 13 is a sectional view of a fractured metacarpal taken during performance of an exemplary method of installing the fixation system of FIG. 1 in the metacarpal, with the pin of the fixation system operatively disposed in the deepest pin-receiving hole of the driver of FIG. 10 and being advanced into the metacarpal through a bore formed in the cortex of the metacarpal, in accordance with aspects of the present disclosure.

FIG. 15 is yet another sectional view of the metacarpal of FIG. 13, taken as in FIGS. 13 and 14 but at a later stage of the method than in FIG. 14, with the pin in the shallowest pin-receiving hole of the driver, advanced to a final position in the bone, and assembled with the collar, which has also been driven into a bore formed in the metacarpal, to attach the pin to bone such that longitudinal travel of the pin is restricted, to retain the pin in the bone, in accordance with aspects of the present disclosure.

FIG. 16 is still another sectional view of the metacarpal of FIG. 13, taken as in FIG. 15 but after completion of the method, namely, with the driver removed and the pin shortened by cutting near the trailing end of the collar, to minimize protrusion of the pin from the collar and/or bone, in accordance with aspects of the present disclosure.

FIG. 17 is a view of another exemplary embodiment of a bone fixation system including a pin and a collar, with the pin and collar having different complementary surface features than in FIG. 1, in accordance with aspects of the present disclosure.

FIG. 18 is a view of yet another exemplary embodiment of a bone fixation system including a pin and a collar, with the pin having a split leading end composed of a shape memory material, in accordance with aspects of the present disclosure.

FIG. 19 is a view of an exemplary embodiment of a bone fixation system including a threaded retainer pivotably connected to a trailing end of a pin and having a fixed longitudinal position along the pin, in accordance with aspects of the present disclosure.

FIG. 19A is a fragmentary, partially sectional view of the system of FIG. 19, taken generally along line 19A-19A of FIG. 19.

FIG. 20 is a view of another exemplary embodiment of a bone fixation system including a threaded retainer pivotably connected to a trailing end of a pin and having a fixed longitudinal position along the pin, in accordance with aspects of the present disclosure.

FIG. 21 is a view of an exemplary embodiment of a bone fixation system including a collar forming a threaded connection with a pin, in accordance with aspects of the present disclosure.

FIG. 22 is a view of another exemplary embodiment of a bone fixation system including a collar forming a threaded connection with a pin, in accordance with aspects of the present disclosure.

DETAILED DESCRIPTION

Figure 7:
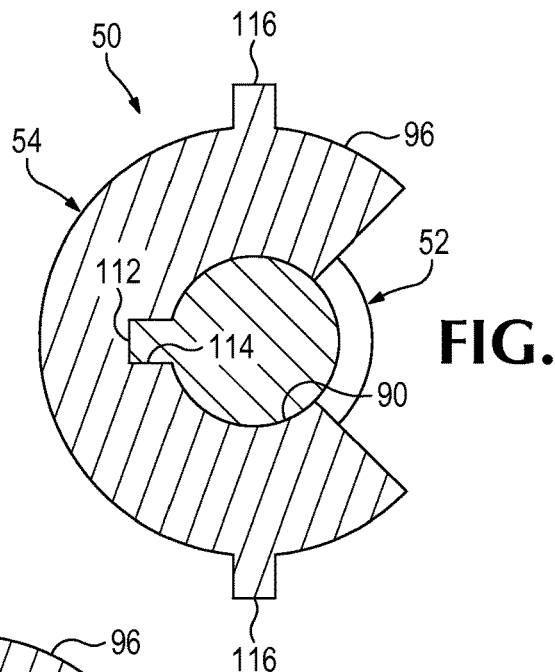
FIG. 7 is a cross-sectional view of another exemplary embodiment of a fixation system including a pin and a collar, taken as in FIG. 4, with the pin having at least one protrusion received in at least one corresponding recess of the collar to restrict pivotal motion of the pin and the collar with respect to one another, and with the collar having one or more protrusions defined by an outer surface of the collar to restrict pivotal motion of the collar and bone with respect to one another, in accordance with aspects of the present disclosure.

The present disclosure provides a system, including methods and devices, for bone fixation with a pin and a collar. In exemplary embodiments, the system may comprise a pin configured to be inserted into a bone, and a deformable collar to retain the pin in the bone. The collar may be configured to be operatively disposed on the pin such that the collar extends more than halfway and less than completely around the pin. The pin and the collar may have complementary surface features that discourage sliding of the collar along a long axis of the pin. In some embodiments, the collar may be configured to be operatively disposed on the pin at a plurality of discrete, alternative axial positions along the long axis of the pin. The pin may be cut to a desired length.

In an exemplary method, at least portion of the pin may be inserted into a medullary cavity of a bone. The pin may be retained in the bone with a retainer that engages the pin and the bone, to prevent the pin from migrating out of the bone. In some embodiments, the retainer may include a collar. In some embodiments, the collar may be a plug that is driven axially and/or translationally into the bone, which may wedge the plug in the bone and attach the pin to the bone. In some embodiments, the pin may be shortened, such as by cutting the pin, to remove a proximal region of the pin.

The present disclosure is related to intramedullary fixation of one or more bones, such as one or more phalangeal, metacarpal, and/or metatarsal bones having one or more fractures, cuts (osteotomies), nonunions, or other discontinuities (such as a joint between the bones at which the bones are to be fused). Installation of any of the devices disclosed herein may be performed using minimally invasive techniques, in contrast to more invasive techniques associated with open reduction/internal fixation (ORIF), such as with a bone plate.

Currently, the main options for fixation of bones of the hands and feet are K-wires or bone plates, which have very different drawbacks. K-wires are popular with surgeons because K-wires are compatible with minimally invasive techniques, have a low cost, and promote biologically-friendly healing. However, surgeons who use K-wires are often frustrated by the associated problems of prominent hardware: the proximal ends of the K-wires are generally left outside the bone and sometimes outside of the skin, which can encourage infection. Also, K-wires limit early motion, can migrate, and typically require a second procedure for their removal. Bone plates, on the other hand, provide very stable fixation and early range of motion, but may produce soft tissue irritation and create soft tissue adhesions from scarring, among other disadvantages. There exists a need for a fixation approach that is functionally intermediate the extremes of K-wires and bone plates.

The present disclosure provides a fixation system including an intramedullary pin, which may be flexible, and a retainer for the pin. The system solves at least some of the problems of traditional K-wire fixation, while still permitting a minimally invasive approach. Any of the embodiments disclosed herein may be inserted in a percutaneous approach and may be sub-osseous, with little or no hardware prominence outside of bone. Furthermore, any of the embodiments may be designed to be cut-to-length, to solve problems related to excess inventory and instruments associated with fixed-length intramedullary devices. Any of the embodiments may be available in a variety of diameters to suit various patient needs.

Further aspects of the present disclosure are described in the following sections: (I) exemplary bone fixation system with a pin and a collar, (II) rotation-resistant pin-and-collar assemblies, (III) exemplary driver for installation of a pin and a collar, (IV) methods of bone fixation with a pin and a collar, (V) composition of system components, (IV) kits, and (VII) examples.

I. Exemplary Bone Fixation System with a Pin and a Collar

This section describes an exemplary bone fixation system 50 including a pin 52 and a collar 54; see FIGS. 1-6.

FIGS. 1 and 2 show an exemplary system 50 for fixation of a small bone (e.g., a bone of the hand or foot) having a discontinuity (such as a fracture). The system may include an intramedullary pin 52 (interchangeably termed an intramedullary spanning element or a nail) and a retainer, which may be in the form of a retaining collar 54 for the pin. Here, collar 54 is structured to function as a plug. The collar mates with the pin and retains the pin in bone, generally by engaging the pin and the bone, to restrict longitudinal movement of the pin with respect to the bone, parallel to a long axis 56 defined by the pin (e.g., to prevent the pin from backing out). The collar thus may provide length control/stability for the bone. The collar, in its retaining role, may or may not restrict rotation of the pin about long axis 56, to provide rotational stability for the pin and/or bone.

Pin 52 may be configured to be inserted into bone only partially. (In other embodiments, the pin may be configured to be inserted completely into bone.) The pin may have a shaft forming a distal portion 58 (interchangeably termed a leading portion) for placement completely into bone. Distal portion 58 may taper to form a tip 64 to facilitate entry into bone (such as entry through a hole formed in the bone). The pin also may form an intermediate portion 60 for placement only partially into bone, and a proximal portion 62 (interchangeably termed a trailing portion) that remains outside the bone. Proximal portion 62 may be grasped or otherwise engaged to permit manipulation of the pin. The entire proximal portion along with a length of intermediate portion 60 that is outside bone may be separated from the rest of the pin during installation. The relative lengths of the distal, intermediate, and proximal portions may be dictated by the length of the bone (or the range of bone lengths for which the pin is configured), the depth of pin insertion, the external length of pin needed or desired for efficient manipulation, and the like.

The pin may be straight (no longitudinal curvature) or curved longitudinally, as shown here, among others. The curvature may be in a single plane (two-dimensional curvature), as shown here, or in multiple planes (three-dimensional curvature). In some embodiments, the curvature may be restricted at least predominantly to distal portion 58, such that intermediate portion 60 and/or proximal portion 62 are linear.

FIGS. 1-3 show further aspects of intermediate portion 60. The immediate portion may have surface features 66 to facilitate mating pin 52 with collar 54 and/or to restrict movement of the collar on the pin, such as about and/or along long axis 56 of the pin. The surface features may be absent from distal portion 58 and proximal portion 62, which each may be cylindrical as shown here, or the surface features also may be formed on either or both of portions 58, 62.

The surface features may include protrusions, notches 68 (interchangeably termed depressions or indentations), or a combination thereof. The surface features may be produced by variations in the diameter of the pin, such as periodic variations that occur at regular intervals along the pin. In other words, the surface features may be spaced uniformly from one another. For example, pin 52 has a longitudinal array of notches 68. Each surface feature may (or may not) be orthogonal to long axis 56. Each surface feature may extend only partially or completely around the long axis of the pin in a plane that is orthogonal to a long axis of the pin. Accordingly, the surface features may or may not be axisymmetric, and may or may not permit the collar to be pivoted about long axis 56. The surface features may form only a finite number of axial positions at which collar 54 is configured to be operatively disposed on pin 52. Axial motion of the collar along the pin at each of the positions may be discouraged by complementary surface features of the pin and collar after the collar is operatively mated with the pin. In the depicted embodiment, each notch 68 forms the center of one of the axial positions at which the collar can be operatively disposed on the pin. For example, FIG. 3 shows collar 54 positioned at a central notch along intermediate portion 60, and alternatively positioned in phantom at two other notches that are proximal and distal (and non-adjacent) to the central notch. As described further below, the collar may or may not be movable axially between adjacent notches without removing the collar from the pin.

Collar 54 has a trailing end 70 opposite a leading end 72, and defines an opening 74 (also called a slot) that extends from the leading end to the trailing end. Opening 74 may be open along one side of the collar from the trailing end to the leading end.

FIGS. 4 and 5 shows cross-sectional views of the collar operatively mated with the pin (FIG. 4) or as the collar is being mated with and deformed by the pin (FIG. 5). The collar may be C-shaped when viewed along a central axis 76 thereof, and may extend at least or more than halfway and less than completely around the pin when operatively received on the pin. In other embodiments, the collar may extend no more than halfway around the pin and/or may not be deformed when the collar is assembled with the pin.

The collar may be configured to operatively receive a longitudinal section 78 of the pin in opening 74 (see FIG. 6). The opening may include a hole 80, which may be centered on central axis 76 (see FIGS. 4 and 5). Longitudinal section 78 may be disposed in hole 80 when the collar is operatively received on the pin. Accordingly, the hole may be described as a seating portion of opening 74. Hole 80 may be open along one side of the collar from trailing end 70 to leading end 72, to form a gap 82. The gap facilitates deformation of the collar, such as when the collar and the pin are being mated with one another. Also, the gap may function as a lateral entryway (interchangeably termed an entry portion or mouth) leading to hole 80. The entryway allows collar 54 to be placed onto pin 52, indicated by a motion arrow at 84 in FIG. 5, from a side of the pin (transverse to the long axis of the pin), such that pin 52 is operatively disposed in hole 80. The entryway may taper toward hole 80 of opening 74. The opening may have a width 86 at the junction between gap 82 and hole 80 (see FIG. 4) that is less than a corresponding diameter 88 (see FIG. 4) of an aligned region of the pin. Accordingly, the collar may be deformed (e.g., elastically) when the collar is urged onto the pin to increase the size of gap 82, particularly to increase width 86 until the width corresponds to the diameter of the pin (compare FIGS. 4 and 5). This deformation may allow the collar to snap into place on the pin. In some embodiments, the collar also or alternatively may be placed onto the pin from at least one end of the pin.

An inner surface 90 of collar 54 (here, the wall of hole 80) may define at least one surface feature, such as a notch or a protrusion 92, that is complementary to one or more surface features defined by pin 52. For example, in the depicted embodiment, protrusion 92 is complementary to each notch 68 of pin 52, which allows the protrusion to be received alternatively in each of the notches. The collar thus can be seated on the pin, with the protrusion in a notch, to at least discourage or restrict movement of the collar in a longitudinal direction of the pin. In some embodiments, the collar may be sufficiently deformable to be forced axially along the pin before the collar is engaged with bone. If sufficiently deformable, the collar may be urged along the pin, to force protrusion 92 out of one notch 68, onto a wider region of the pin, and then into the next notch 68 (or a plurality of successive notches 68) along the pin, to reposition the collar axially. In some embodiments, the collar may be seated on the pin via interaction of at least one protrusion with at least one notch, to restrict axial motion of the collar along the pin and/or pivotal motion of the collar about the pin (see Section II). In some embodiments, the collar may be freely slideable on the pin, along a long axis thereof, until the collar is engaged with bone.

Collar 54 may have a general taper from trailing end 70 to leading end 72 to form a generally conical profile (see FIG. 6). In other words, the collar may narrow toward the leading end, such that the leading half of the collar has a smaller average diameter than the trailing half of the collar. This geometry facilitates wedging the collar into an appropriately sized bore formed in bone, which may radially compress the collar against the pin. Compression of the collar against the pin may restrict axial movement of the collar along the pin. In other embodiments, the collar may lack the general taper of the depicted embodiment.

One or more ridges 94 (also called teeth) may be formed on a bone-contacting outer surface 96 of the collar (see FIG. 6). The ridges may be asymmetrical, with a less steeply-sloped leading face 98 to facilitate translational advancement of the collar into bone, and a steeper trailing side 100 to resist reverse movement (backing out) of the collar out of bone. Each ridge 94 (e.g., a crest thereof) may extend about central axis 76 of the collar, such as extending in a plane that is orthogonal to the central axis. The collar also may have one or more longitudinal protrusions (e.g. fins) and/or indentations (e.g., slots) respectively formed on or in outer surface 96 (see Section II). The protrusions/indentations may function to restrict pivotal movement of the collar and bone relative to one another. Alternatively, or in addition, the collar may have a flat side formed on its outer surface to restrict pivotal movement. In other embodiments, collar 54 may have one or more helical ridges defined by its outer surface.

Collar 54 may retain pin 52 in bone without any (helical) threaded engagement between collar 54 and pin 52 and/or without any (helical) threaded engagement between the collar and bone. Threaded engagement, as used herein, is any engagement that involves a helical thread, such as an external thread or an internal thread.

A retainer of the present disclosure, such as collar 54, may have any suitable structure to perform the intended purpose of attaching the pin to bone. The retainer may be configured to be disposed on/around and/or at least partially in the pin. The retainer may have only an external thread (e.g., see Example 3), an internal thread, both an internal thread and an external thread (e.g., see Example 4), or no thread (see above). The retainer may be operatively disposed on the pin (i.e., operatively assembled with the pin) before or after a portion of the pin enters bone. The retainer may be disposed around the pin with the retainer extending more than halfway or completely around the circumference of the pin. The retainer may be a single piece or two or more pieces.

Further aspects of exemplary retainers are described elsewhere herein, and in U.S. Provisional Patent Application Ser. No. 62/016,883, filed Jun. 25, 2014, which is incorporated herein by reference.

II. Rotation-resistant Pin-and-Collar Assemblies

Figure 8:
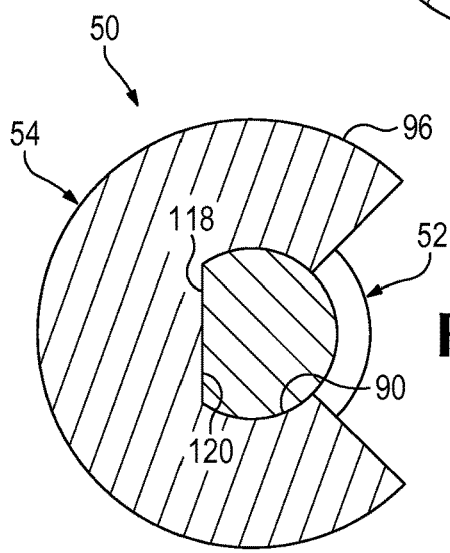
FIG. 8 is a cross-sectional view of still another exemplary embodiment of a fixation system including a pin and a collar, taken as in FIG. 4, with the pin and the inner surface of the collar defining corresponding flats that restrict pivotal motion of the pin and the collar with respect to one another, in accordance with aspects of the present disclosure.
Figure 9:
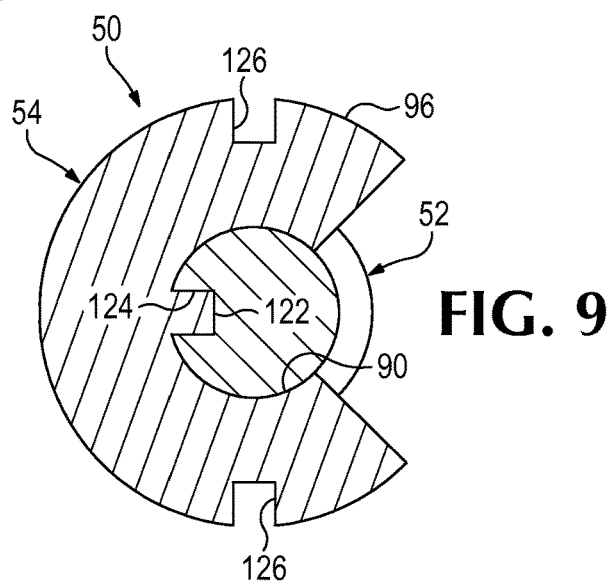
FIG. 9 is a cross-sectional view of yet another exemplary embodiment of a fixation system including a pin and a collar, taken as in FIG. 4, with the inner surface of the collar defining at least one protrusion received in at least one corresponding recess of the pin to restrict pivotal motion of the pin and the collar with respect to one another, and with the collar having one or more longitudinal indentations defined by an outer surface of the collar to restrict pivotal motion of the collar and bone with respect to one another, in accordance with aspects of the present disclosure.

This section describes exemplary assemblies of a pin 52 and a collar 54 that are resistant to rotation relative to one another and/or relative to bone; see FIGS. 7-9. The pins and collars disclosed in the section may include any suitable combination of features disclosed for fixation systems (e.g., fixation system 50) in Section I or elsewhere herein.

Collar 54 may impart rotational stability to pin 52 and/or bone by restricting rotation of the pin and the bone relative to one another about the long axis of the pin and/or restricting rotation of the collar and the bone relative to one another. Rotational stability may be created by frictional contact of the collar and pin with one another and/or frictional contact of the collar and bone with one another. Alternatively, or in addition, rotational stability may be created by a noncircular cross section of the pin and/or collar (i.e., a noncircular cross section defined by inner surface 90 or outer surface 96 of the collar and/or the exterior surface of the pin. For example, the collar and/or pin may define one or more protrusions and/or recesses. Each protrusion may, for example, project radially outward, and each recess may, for example, subside radially inward. The protrusion may be a longitudinal ridge (also called a fin or a flange) and/or the recess may be a longitudinal furrow (also called a slot) each elongated at least generally parallel (e.g., within about 20 degrees or within about 10 degrees of parallel) to the central axis of the collar or the long axis of the pin.

FIG. 7 shows an exemplary embodiment of a fixation system 50 including a pin 52 and a collar 54 each having one or more protrusions and/or recesses (also called indentations) to resist rotation. The pin has at least one protrusion 112 (here, a longitudinal flange) received in at least one corresponding recess 114 (here, a longitudinal furrow) defined by inner surface 90 of the collar to restrict pivotal motion of the pin and the collar with respect to one another. Also, collar 54 has one or more protrusions 116 (here, longitudinal flanges) defined by outer surface 96 of the collar to restrict pivotal motion of the collar and bone with respect to one another.

FIG. 8 shows another exemplary embodiment of a fixation system 50 including a pin 52 and a collar 54 with rotation-resistant features. More particularly, the exterior surface of the pin and an inner surface 90 of the collar define corresponding flats 118, 120 that restrict pivotal motion of the pin and the collar with respect to one another about the long axis of the pin. Stated differently, the pin may have a flat side that is engaged by a corresponding flat surface region defined by the inner surface of the collar.

FIG. 9 shows yet another exemplary embodiment of a fixation system 50 including a pin 52 and a collar 54 with rotation-resistant features. An inner surface 90 of collar 54 defines at least one protrusion 122 (here, a longitudinal flange) received in at least one corresponding recess 124 (here, a longitudinal furrow) of the pin to restrict pivotal motion of the pin and the collar with respect to one another about the long axis of the pin. Collar 54 also may have one or more indentations 126 (here, longitudinal furrows) defined by an outer surface 96 of the collar to restrict pivotal motion of the collar and bone with respect to one another about the long axis of the pin.

III. Exemplary Driver for Installation of a Pin and a Collar

This section describes an exemplary driver 130 for introducing pins and collars into bone; see FIGS. 10-12.

FIGS. 10 and 11 show driver 130 with pin 52 operatively received in the driver. The driver may be utilized to drive the pin and/or a collar 54 into bone, by application of axial force to the pin/collar, optionally by striking the driver one or more times.

Driver 130 may have a head 132 connected to a body 134 (interchangeably termed a shaft). The head may be wider than the body, and may form a proximal face 136 (a striking target) that can be impacted with a hand (e.g., with the proximal portion (the heel) of the surgeon's palm) or a striking tool (such as a mallet) to drive the pin into bone. The head also may function as a handle for manipulating the driver, such as to pivot the driver as axial force is being applied to the driver. The driver also may be capable of transmitting torque to the pin (see below), which may, for example, allow some directional control of the distal tip of the pin. In some embodiments, the driver may be configured to be attached to the pin, such as via a set screw connected to the body of the driver, among others.

The driver may be configured to receive different proximal lengths of the pin. For example, in the depicted embodiment, the driver defines a plurality of holes 138, 140, and 142 (such as blind holes) that extend along parallel paths into body 134 from a distal end thereof. The holes may have different lengths/depths to receive different length portions of the pin, in each case until the trailing end of the pin contacts an inner end 144 of each hole. For example, in the depicted embodiment, each hole 138, 140, or 142 receives proximal portion 62 of pin 52. However, hole 138 is configured to receive substantially all of intermediate portion 60 of the pin; hole 140 is not as deep as hole 138 and receives only about one-half of the length of intermediate portion 60; and hole 142 is still shallower and receives less than one-fourth the length of intermediate portion 60. Each hole may be sized transversely according to the diameter of the pin, to provide a relatively close fit that minimizes lateral play of the pin, while being wide enough to allow the pin to be easily placed into and removed from the hole. In other embodiments, the driver may have one, two, four, or more holes. One or more of the holes may be optionally utilized only when the pin is to be driven farther into the bone.

The pin may be driven into a bone in stages with the pin sequentially disposed in holes 138, 140, and 142 of decreasing depth (also see Section IV). The pin may be placed first into deepest hole 138, and the tip of the pin placed into a bore formed in the bone. The pin then may be driven into the bone with axial force (e.g., continuous or pulsatile force) applied via driver 130 until the pin enters the medullary cavity and/or the driver closely approaches or contacts the bone. The process then may be repeated with the pin disposed in intermediate-depth hole 140 and then shallowest hole 142, to drive the pin farther into bone. One or more of the shallower holes optionally may not be utilized if the pin can be driven far enough without them.

The driver also may have a nose 146 projecting distally from the distal end of body 134 and centered on one of the holes, such as shallowest hole 142, with the outer end of hole 142 defined by the nose. The distal end of nose 146 may be configured to contact and transmit force to the trailing/proximal end of collar 54. The nose may or may not be sized and shaped to permit the nose to contact and/or at least partially enter a bore formed in the bone. For example, the nose may have a diameter at its leading end that is about the same as or less than the diameter of the trailing end of collar 54, which may allow the nose to drive the collar to a recessed position with respect to the surrounding surface area of the bone. Alternatively, the nose at its leading end may have a diameter that is greater than the diameter of the trailing end of the collar, such that contact of the nose with the exterior of the bone stops advancement of the nose and positions the collar flush with the surface of the bone. In any event, the collar and the pin may be advanced axially as a unit, as the collar is driven into the bone, until the collar is fully seated in the bone (also see Section IV). The collar may be driven into bone translationally without any substantial rotation of the collar. For example, the collar may be driven into bone while the collar turns less than one or less than one-half revolution, if any.

FIG. 12 shows a cross-sectional view of another exemplary embodiment of a driver 130 and a pin 52. Here, the pin and the driver are not pivotable relative to one another, after the pin has been operatively received by the driver, such that the driver can transmit torque to the pin. For example, a proximal end of the pin and the inner end of each hole 138, 140, and 142 may have corresponding noncircular shapes, such as forming respective, corresponding flats 148, 150 to restrict pivotal motion of the pin and driver relative to one another. Flat 148 may be formed on any suitable portion of pin 52, including an intermediate portion 60 that mates with a collar (e.g., see FIG. 8).

IV. Methods of Bone Fixation with a Pin and a Collar

This section describes exemplary methods of bone fixation with a pin retained in bone with a retainer, such as a collar. An exemplary method is illustrated with system 50 of FIGS. 1-6; see FIGS. 13-16. The method steps described in this section may be performed in any suitable order and combination, using any combination of the devices (and/or device features) of the present disclosure.

At least one bone to be fixed may be selected. The at least one bone may be a single bone having at least one discontinuity (a fracture, cut, nonunion, or the like), or two or more bones (for fusion to each other) connected to one another at one or more joints. The at least one bone selected may include a bone of the arms (a humerus, radius, or ulna), the legs (a femur, tibia, or fibula), the wrist (carpals), hands (a phalange or metacarpal), ankle (a calcaneus or talus or tarsal), feet (a phalange or metatarsal), a clavicle, a rib, a scapula, a pelvis, or the like. The at least one bone selected may be described as a small bone, such as a bone of the hands or feet.

A pin may be selected for fixation of the at least one bone. Also, a retainer, such as a collar, may be selected for retaining the pin in the least one bone. The pin (or retainer) may be selected from a set of pins (or retainers) of different diameter, length, longitudinal shape, and/or the like.

A site for entry of the pin into bone may be selected. The site may be near or at the end of the bone. In some embodiments, the site may be near a junction region where a side and an end of the bone meet.

The site may be prepared for entry of the pin. For example, a medullary cavity of the bone may be accessed by forming a hole through the cortex of the bone at the site. The hole may be created with any suitable hole-forming tool such as an awl, a drill, a punch, a sharp end of the pin itself, or the like. In some embodiments, a bore to receive a retainer, such as a collar, also or alternatively may be formed in, and optionally through, the cortex at the site. The bore may be sized in correspondence with an outer diameter of the collar, generally slightly smaller than the outer diameter, such that collar will fit tightly in the bore. The bore may be formed before or after any portion of the pin has entered bone.

The pin may be inserted into the at least one bone, such that at least a portion of the pin enters the at least one bone at the selected and prepared site. The pin may be inserted along the at least one bone, such that the pin is aligned with a medullary cavity of the bone. The pin may be inserted any suitable distance into the bone, such as a majority of the length of the bone, such that the pin extends between opposite end regions of the bone. Insertion of the pin may be driven percussively with one or more pulsatile axial loads applied directly or indirectly to the pin with a striking tool or the surgeon's hand, among others.

The retainer may be assembled with the pin. For example, the retainer may be placed onto the pin. Placement may be from the side or the end of the pin, or the retainer and pin may be supplied together to the surgeon as a pre-assembled device. The retainer may be a collar that is placed onto the pin, such as snapped on transversely, at one of a plurality of alternative, discrete positions along the pin. In some embodiments, the collar may be placed onto the pin after the pin has been advanced across a discontinuity defined by the at least one bone, and with the pin close to or at a final position in the bone.

The retainer may be inserted into the bone, such that at least a portion of the retainer enters the bone. For example, the retainer may be a collar that is driven into the bore in the bone by an axial force (such as continuous or pulsatile force), by turning the collar, or the like. In some embodiments, the collar may be advanced until it is flush or recessed with respect to the bone, or until a head (if present) of the collar is engaged with an exterior of the bone. Driving the collar into the bone and/or bore thereof may radially compress the collar inwardly towards a central axis of the collar.

The pin may be sectioned to reduce its length (i.e., to shorten the pin). Sectioning may remove an external longitudinal portion of the pin. Sectioning may be performed by, for example, cutting or breaking the pin. In some cases, the same driver used to drive the collar into bone may be utilized to break off the pin near the trailing end of the collar.

FIGS. 13-16 depict exemplary configurations produced during performance of an exemplary method of fixing bone with system 50 of FIGS. 1-6.

FIG. 13 shows an exemplary bone 160 having a discontinuity 162 and already prepared to received pin 52. Bone 160 is a metacarpal of the left hand and has sustained a fracture that creates the discontinuity. Metacarpal 160 articulates with a phalange 164 distally and with one or more carpals 166 proximally. The metacarpal has a cortex 168 surrounding a medullary cavity 170, each of which is shown schematically. The medullary cavity has been accessed at least in part by forming a bore 172 through cortex 168. The bore may be extra-articular, being formed near but outside of a joint 174 at which metacarpal 160 articulates with phalange 164, or may overlap the joint.

Pin 52 extends into driver 130 and bone 160. The proximal portion of the pin is operatively disposed in deepest pin-receiving hole 138 of driver 130, and extends into medullary cavity 170 through bore 172. A majority of distal portion 58 has been placed inside metacarpal 160.

Figure 14:
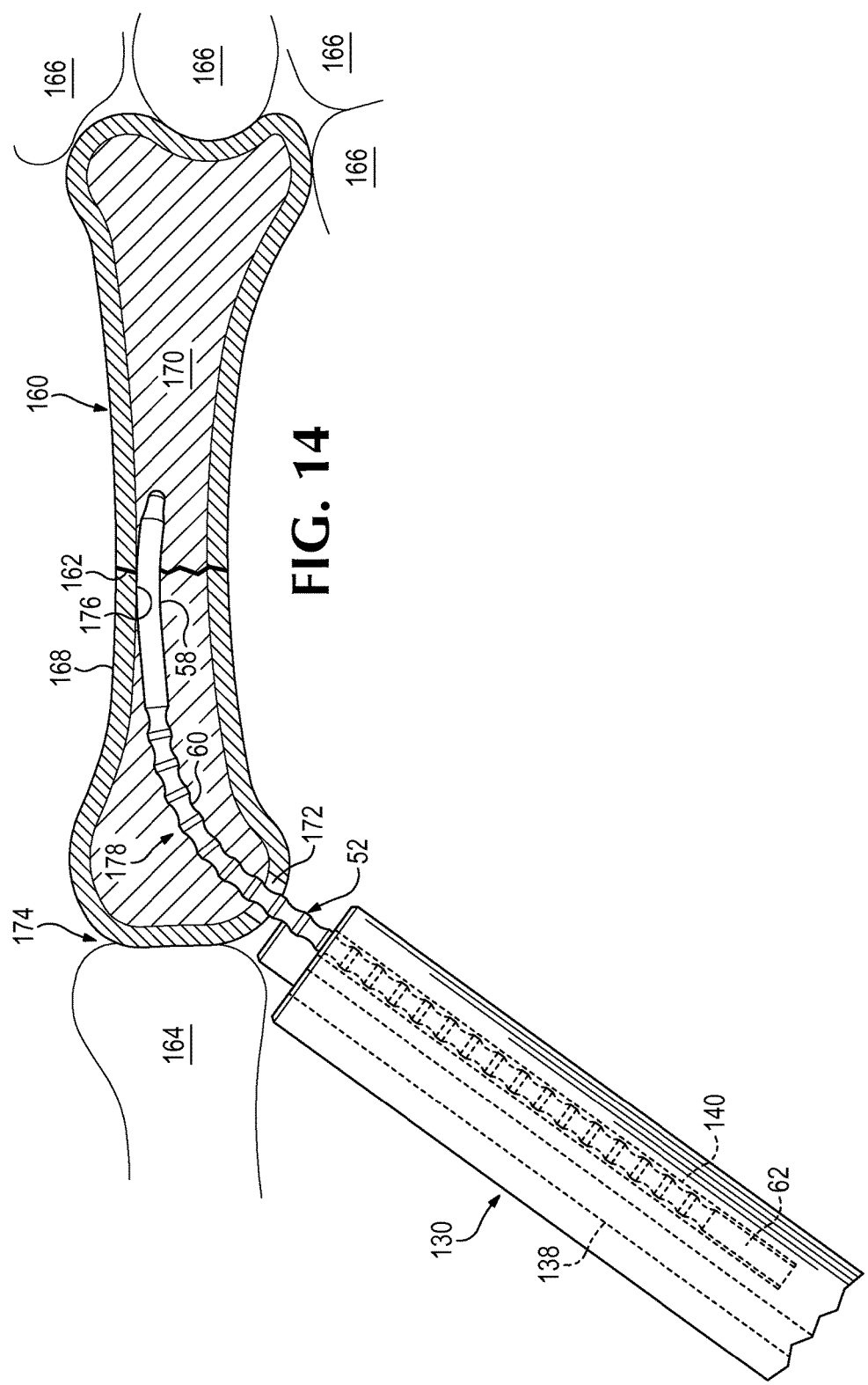
FIG. 14 is another sectional view of the metacarpal of FIG. 13, taken as in FIG. 13 but at a later stage of the method, with the pin in the intermediate-depth pin-receiving hole of the driver, deformed longitudinally by contact with the cortex of the metacarpal bone, and spanning the fracture of the metacarpal with a leading portion of the pin, in accordance with aspects of the present disclosure.

FIG. 14 shows metacarpal 160, pin 52, and driver 130 at a later stage of the method. Proximal portion 62 of the pin has been moved from deepest pin-receiving hole 138 to intermediate-depth pin-receiving hole 140. Part of notched intermediate portion 60 has been advanced into metacarpal 160, and distal portion 58 now spans fracture 162. Pin 52 has been deformed longitudinally by contact with an inner wall region 176 of cortex 168, such that the pin has a longitudinal bend or curved region 178 created by the insertion process.

FIG. 15 shows metacarpal 160, pin 52, and driver 130 at an even later stage of the method. Proximal portion 62 of the pin has been moved from intermediate-depth pin-receiving hole 140 to shallowest pin-receiving hole 142. The pin has been advanced to its final position in metacarpal 160, such that tip 64 of the pin is near the opposite end of the bone.

Collar 54 also has been assembled with notched intermediate portion 60 of pin 52, to form a pin-and-collar assembly, and then the assembly has been driven into metacarpal 160. The collar is at least partially disposed in bore 172 and is engaged tightly with a wall of the bore. Nose 146 of the driver is still abutted with trailing end 70 of collar 54 after transmitting force to the collar that has urged the collar into the metacarpal. The nose is too wide in the depicted embodiment to enter bore 172. Accordingly, trailing end 70 of the collar is positioned flush with the surrounding exterior surface region of the metacarpal. The collar prevents longitudinal movement of pin 52 with respect to metacarpal 160, and pin 52 is held by collar 54 in bent configuration 178 created by pin insertion.

At this stage, driver 130 may be used to shorten the pin. The driver may be manipulated to break off a proximal length of the pin. For example, the driver may be backed up a short distance (e.g., one millimeter) to create a gap between the distal end of nose 146 and the trailing end of the collar. The driver then may be pivoted (e.g., rocked back and forth) about an axis orthogonal to the pin near the distal end of nose 146 until the pin breaks.

FIG. 16 shows metacarpal 160, pin 52, and collar 54 after completion of the method. The driver has been removed. Also, pin 52 has been shortened by cutting the pin near trailing end 70 of the collar, to create a new proximal end 180 of the pin and minimize protrusion of the pin from the collar and/or bone.

V. Composition of System Components

A pin and a retainer for the pin may have any suitable composition. Each may be formed of any suitable biocompatible material(s) and/or bioresorbable (bioabsorbable) material(s). Illustrative biocompatible materials that may be suitable for a pin and/or a retainer include (1) metal (for example, titanium or titanium alloy, cobalt-chrome alloy, stainless steel, etc.); (2) polymer/plastic (for example, ultrahigh molecular weight polyethylene (UHMWPE), polymethylmethacrylate (PMMA), polytetrafluoroethylene (PTFE), polyetheretherketone (PEEK), and/or PMMA/polyhydroxyethylmethacrylate (PHEMA)); (3) bioresorbable material or polymer/plastic (for example, polymers of α-hydroxy carboxylic acids (e.g., polylactic acid (such as PLLA, PDLLA, and/or PDLA), polyglycolic acid, lactide/glycolide copolymers, etc.), polydioxanones, polycaprolactones, polytrimethylene carbonate, polyethylene oxide, poly-β-hydroxybutyrate, poly-β-hydroxypropionate, poly-δ-valerolactone, poly(hydroxyalkanoate)s of the PHB-PHV class, other bioresorbable polyesters, and/or natural polymers (such as collagen or other polypeptides, polysaccharides (e.g., starch, cellulose, and/or chitosan), any copolymers thereof, etc.)); (4) bone material or bone-like material (e.g., bone chips, calcium phosphate crystals (e.g., hydroxyapatite, carbonated apatite, etc.)); or (5) any combination thereof.

The pin and the retainer for the pin may be formed of the same or different materials. For example, each may be formed of metal, each may be formed of plastic (polymer), or the pin may be formed of metal and the retainer may be formed of plastic (or vice versa), among others.

VI. Kits

The fixation system may be provided as a system/kit including at least one pin, at least one retainer, a driver for the pin and/or retainer, a drill bit (to form a bore to receive the collar), instructions for use, or the like. The system/kit may provide two or more different choices for at least one of the components. For example, the system/kit may include a set of two or more pins of different length, diameter, flexibility, longitudinal shape, or a combination thereof, among others; and/or a set of two or more retainers (such as collars) of different diameter, length, or the like.

VII. Examples

The following examples describe selected aspects and embodiments of the present disclosure including exemplary bone fixation systems, and methods of installing the systems to fix bone. The aspects and features of the systems, devices, and methods described in each of these examples may be combined with one another and with aspects and features of the systems, devices, and methods described elsewhere in the present disclosure, in any suitable combination. These examples are intended for illustration and should not limit the entire scope of the present disclosure.

Example 1

Bone Fixation System with a Pin having Raised Surface Features

This example describes an exemplary bone fixation system 190 including a flexible pin 52 having a longitudinal, regular array of surface features 192 formed as longitudinally-convex protrusions 194; see FIG. 17.

Protrusions 194 may be formed integrally with a cylindrical shaft 196 of the pin and may be defined by an increase in diameter over that of the shaft. Adjacent protrusions 194 may share a boundary or may be separated by a cylindrical spacer region 198 that has the same diameter as, or a smaller diameter than, the shaft. In any event, notches 200 may be defined between adjacent pairs of protrusions 194.

System 190 may include an open-slotted collar 54 generally as described above for collar 54 of system 50 (e.g., see FIGS. 1-6). Collar 54 is designed to fit onto and be seated on pin 52 at one of a plurality of discrete, alternative axial positions defined by surface features 192 of the pin. More particularly, collar 54 has a pair of inside collar protrusions 202 each configured to be received in a notch between an adjacent pair of pin protrusions 194. Also, collar 54 defines a circumferential indentation 204 between collar protrusions 202 and configured to receive one of pin protrusions 194.

Example 2

Bone Fixation System with a Pin having a Split Tip

This example describes an exemplary bone fixation system 210 including a pin 52 having a distal end portion 212 that is split longitudinally; see FIG. 18.

The distal end portion may form a pair of legs 214, 216 that, when splayed, impart rotational stability to the pin. The legs may be formed of a shape memory material, such as nitinol. One or both legs may be curved longitudinally or may be straight. One or both legs may change shape after the pin is placed into bone, to expand a leading end region of the pin. For example, the legs may be collapsed, namely, arranged parallel to one another and optionally abutted along their lengths, before and during pin placement, but may bend away from each other to spread apart and return to a "remembered" shape when the pin is heated sufficiently inside the medullary cavity (such as by the body temperature of the pin recipient).

Example 3

Bone Fixation System with a Pivotable, Threaded Retainer

This example describes exemplary bone fixation systems including a pin pivotably connected to an externally-threaded retainer; see FIGS. 19, 19A, and 20.

FIGS. 19 and 19A show a system 220 including a pin 222 and a threaded retainer 224. Retainer 224 interchangeably may be termed a cap or a screw. The retainer may have an external thread 226 for engagement with bone, such as cortical bone.

The retainer is pivotably connected to a trailing end of pin 222 via a ball-and-socket joint 228 such that the retainer can be rotated about the long axis of the pin. In other words, the retainer has a substantially fixed longitudinal position along the pin. Pin 222 forms a ball portion 230 and retainer 224 forms a socket 232 of joint 228. In exemplary embodiments, the retainer may be swaged, indicated by an arrow at 234 in FIG. 19A, onto ball portion 230, to connect the pin to the retainer. The retainer may extend proximally from the pin and may define a driver-engagement structure 236, such as a hexagonal depression, a single slot or pair of slots, one or more external facets, or the like, for engagement by a driver than turns the retainer. The retainer also may have a head 238 that is not externally-threaded.

Bone fixation system 220 may be installed as follows. Pin 222 may be placed into a bore formed in a cortical region of the bone, with retainer 224 pre-connected to the pin. The pin may be advanced longitudinally (e.g., at least generally translationally) until retainer 224 contacts the bone at the bore. The retainer then may be turned to drive the threaded portion of the retainer into the hole, while advancing connected pin 222 by the same distance. Head 238 may be stopped from entering the bone by contact with an exterior surface region of the bone about the bore, such that the head is engaged with the exterior of the bone and remains outside the bone. Pin 222 may have a fixed length that is not changed during installation (such as by cutting the pin). In other embodiments, head 238 may be omitted and the retainer may be driven to a flush or recessed position with respect to the bone. In other embodiments, retainer 224 may be connected to the pin after the pin has been placed into bone.

FIG. 20 shows another exemplary bone fixation system 240 including a pin 242 and a threaded retainer 224 pivotably connected to the pin via a ball-and-socket joint 228, as described above for system 220 (see FIGS. 19 and 19A). Pin 242 may have one or more longitudinal flanges 246 formed on a wider trailing region 248 of the pin. The pin also has a narrower leading region 250.

Example 4

Bone Fixation System with a Pin Threaded to a Collar

This example describes exemplary bone fixation systems including a pin in threaded engagement with a collar; see FIGS. 21 and 22.

FIG. 21 shows an exemplary bone fixation system 260 including an externally threaded pin 262 and a collar 264 forming a threaded connection with the pin. Pin has an external thread 266 extending along any suitable portion of the pin. For example, in the depicted embodiment, a distal end portion 268 of the pin is nonthreaded. (An alternative shape for the distal end portion is shown in phantom.)

Collar 264 may be described as a threaded cap and may be formed of plastic or metal, among others. The collar has an internal thread 270 that is complementary to external thread 266 of the pin, to attach the collar to the pin, and an external thread 272 to engage bone, such as cortical bone, to attach the collar to bone. The collar may have a head 274 configured to be engaged by a driver that turns the collar. The head may be configured to remain outside bone, and may form a shoulder 276 (interchangeably termed a stop) at the junction between the head and an externally-threaded shaft of the collar. In other embodiments, the head may enter the bone, may be externally threaded, or may be absent.

Pin 262 may be rotationally driven into bone by threaded advancement. The pin may have a driver engagement structure 278 defined at a trailing end of the pin, for use with a rotational driver.

FIG. 22 shows another exemplary bone fixation system 280 including an externally threaded pin 282 and a collar 284 forming a threaded connection with the pin. Pin 282 has an external thread 286 that extends to the distal end of the pin. Collar 284 has a head 288 defining a driver-engagement structure 290.

Example 5

Selected Embodiments I

This example describes selected embodiments of a bone fixation system including a pin and a retainer for the pin, and methods of using the bone fixation system to fix bone, such as a bone of a hand or foot. The selected embodiments are presented as a series of numbered paragraphs.

1. A system of bone fixation, comprising: (A) a pin configured to be inserted into a bone; and (B) a collar to attach the pin to the bone.

2. The system of paragraph 1, wherein the pin has opposing ends, and wherein the collar is configured to be placed onto the pin at a position intermediate the opposing ends of the pin.

3. The system of paragraph 1 or 2, wherein the pin defines a long axis, and wherein the collar is configured to be placed onto the pin in a direction transverse to the long axis.

4. The system of paragraph 2 or 3, wherein the collar is configured to be placed onto the pin at a plurality of discrete, alternative axial positions, such that the collar is seated on the pin and resistant to slippage in an axial direction of the pin.

5. The system of any of paragraphs 2 to 4, wherein the collar is configured to be snapped onto the pin from a side of the pin.

6. The system of any of paragraphs 2 to 5, wherein the collar is configured to deform reversibly as the collar is placed onto the pin.

7. The system of any of paragraphs 1 to 6, wherein the collar includes an outer surface forming one or more asymmetrical ridges that selectively restrict movement of the collar out of bone relative to into bone.

8. The system of any of paragraphs 1 to 7, wherein the pin has a plurality of surface features configured to restrict the collar from sliding longitudinally on the pin.

9. The system of paragraph 8, wherein the surface features include a plurality of notches.

10. The system of paragraph 8 or 9, wherein the pin has a variable diameter that forms the surface features.

11. The system of paragraph 10, wherein the variable diameter varies regularly along at least a portion of the pin.

12. The system of any of paragraphs 8 to 11, wherein each surface feature extends at least partway around the pin on a path arranged orthogonally to a long axis defined by the pin.

13. The system of any of paragraphs 1 to 12, wherein the collar has a leading end opposite a trailing end, and wherein the collar tapers toward the trailing end.

14. The system of any of paragraphs 1 to 13, wherein the collar is pivotable on the pin about a long axis defined by the pin, at least before the collar attaches the pin to bone.

15. The system of any of paragraphs 1 to 14, wherein the collar is configured to be slideable longitudinally on the pin before the collar attaches the pin to the bone.

16. The system of paragraph 1, wherein the collar has an internal thread for threaded engagement with the pin such that turning the collar drives the collar along a long axis defined by the pin.

17. The system of paragraph 16, wherein the collar is configured to be placed onto the pin from an end of the pin.

18. The system of paragraph 1, wherein the collar has an external thread and is pivotably connected to the pin for rotation of the collar about a long axis defined by the pin without travel of the collar along the long axis.

19. The system of paragraph 1, wherein an inner surface of the collar and a surface of the pin define features that engage each other to restrict pivotal movement of the collar and pin relative to one another.

20. A method of bone fixation, the method comprising: (A) inserting a pin into a bone; (B) placing a collar onto the pin; and (C) attaching the pin to the bone with the collar.

21. The method of paragraph 20, further comprising a step of shortening the pin.

22. The method of paragraph 21, wherein the step of shortening the pin shortens the pin irreversibly.

23. The method of paragraph 22, when the step of shortening the pin includes a step of cutting or breaking the pin.

24. The method of any of paragraphs 21 to 23, wherein the step of shortening the pin is performed after the step of placing a collar onto the pin.

25. The method of paragraph 24, wherein the step of shortening the pin is performed after the step of attaching the pin to the bone.

26. The method of any of paragraphs 20 to 25, wherein the pin has opposing ends, and wherein the step of placing the collar onto the pin includes a step of placing the collar onto the pin at a position intermediate the opposing ends.

27. The method of any of paragraphs 20 to 26, wherein the pin defines a long axis, and wherein the collar is placed onto the pin in a direction transverse to the long axis.

28. The method of any of paragraphs 20 to 27, wherein the step of placing a collar onto the pin includes a step of reversibly deforming the collar.

29. The method of paragraph 28, wherein the step of reversibly deforming the collar includes a step of snapping the collar onto the pin.

30. The method of any of paragraphs 20 to 29, wherein the pin has a surface feature configured to contact at least one surface feature defined by an inner surface region of the collar to restrict longitudinal motion of the collar on the pin.

31. The method of any of paragraphs 20 to 30, wherein the step of inserting a pin into a bone includes a step of percussively driving at least a portion of the pin into a bone.

32. The method of paragraph 31, wherein the step of percussively driving at least a portion of the pin into a bone includes a step of striking a driver that is operatively positioned to drive the pin.

33. The method of paragraph 32, wherein the driver defines a plurality of holes of different depth, and wherein the step of percussively driving at least a portion of the pin into a bone is repeated with the pin disposed in two or more of the holes.

34. The method of any of paragraphs 20 to 33, wherein the step of attaching the pin to the bone includes a step of percussively driving at least a portion of the collar into the bone.

35. The method of paragraph 34, wherein the step of percussively driving at least a portion of the collar into the bone causes the collar and the pin to travel as a unit.

36. The method of paragraph 34 or 35, wherein the step of percussively driving at least a portion of the collar into the bone includes a step of wedging the collar into the bone.

37. The method of paragraph 20, wherein the step of attaching the pin to the bone includes a step of driving at least a portion of the collar into threaded engagement with the bone.

38. The method of any of paragraphs 20 to 37, wherein a leading end region of the pin is split longitudinally.

39. The method of paragraph 38, wherein the leading end region of the pin has a pair of legs, and wherein at least one of the legs is configured to move away from the other leg of the pair of legs after the pin is placed into the bone.

40. The method of any of paragraphs 20 to 39, wherein the pin has longitudinal curvature.

41. The method of any of paragraphs 20 to 39, wherein the pin is straight.

42. The method of any of paragraphs 20 to 41, wherein the bone includes a phalange, a metacarpal, a metatarsal, or a clavicle.

43. The method of any of paragraphs 20 to 42, wherein the bone has a discontinuity, and wherein the step of inserting a pin causes the pin to span the discontinuity.

44. The method of any of paragraphs 20 to 43, wherein the step of inserting a pin arranges the pin longitudinally in the bone.

Example 6

Selected Embodiments II

This example describes selected embodiments of a bone fixation system including a pin and a retainer for the pin, and methods of using the bone fixation system to fix bone, such as a bone of a hand or foot. The selected embodiments are presented as a series of numbered paragraphs.

1. A system for bone fixation, comprising: (A) a pin configured to be inserted into a bone; and (B) a deformable collar to retain the pin in the bone; wherein the collar is configured to be operatively disposed on the pin such that the collar extends more than halfway and less than completely around the pin.

2. The system of paragraph 1, wherein the collar has a first end opposite a second end and defines a hole extending through the collar from the first end to the second end, wherein the hole is open on one side of the collar from the first end to the second end to form a gap that is contiguous to the hole, and wherein a size of the gap is configured to change as the collar is being operatively disposed on the pin.

3. The system of paragraph 1 or 2, wherein the pin defines a long axis, and wherein the collar is configured to be operatively disposed on the pin by movement of the pin and the collar relative to one another transverse to the long axis.

4. The system of any of paragraphs 1 to 3, wherein the pin is formed of metal and the collar is formed of polymer.

5. The system of any of paragraphs 1 to 4, wherein the pin has a least one surface feature configured to discourage sliding of the collar along a long axis of the pin after the collar is operatively disposed on the pin.

6. The system of paragraph 5, wherein the at least one surface feature includes a longitudinal array of notches or protrusions defined by the pin, and wherein each notch or protrusion extends at least partway around the long axis of the pin in a plane that is orthogonal to the long axis of the pin.

7. The system of paragraph 5 or 6, wherein the at least one surface feature is formed at least in part by a varying diameter of the pin, wherein the collar defines a hole in which a section of the pin is received when the collar is operatively disposed on the pin, and wherein a diameter of the hole varies along the hole.

8. The system of any of paragraphs 1 to 7, wherein the collar is configured to be operatively disposed on the pin at a plurality of discrete, alternative axial positions along a long axis of the pin.

9. The system of any of paragraphs 1 to 8, wherein the collar includes an outer surface forming one or more asymmetrical ridges that selectively restrict translational movement of the collar out of bone relative to into bone.

10. A system for bone fixation, comprising: (A) a pin configured to be inserted into a bone; and (B) a collar to retain the pin in the bone, the collar having a first end opposite a second end and defining a hole extending through the collar from the first end to the second end, the hole being open along one side of the collar from the first end to the second end to form a lateral entryway to the hole, wherein the collar is configured to be deformed by a section of the pin entering the hole via the lateral entryway from outside the collar.

11. The system of paragraph 10, wherein the lateral entryway tapers toward the hole.

12. The system of paragraph 10 or 11, wherein the pin has a least one surface feature configured to discourage sliding of the collar along a long axis of the pin.

13. The system of paragraph 12, wherein the at least one surface feature includes a plurality of discrete notches.

14. The system of paragraph 13, wherein a diameter of the hole of the collar varies along the hole in correspondence with one of the notches.

15. The system of any of paragraphs 10 to 14, wherein the collar is configured to be operatively disposed on the pin at only a plurality of discrete, alternative axial positions along a long axis of the pin.

16. The system of any of paragraphs 10 to 15, wherein the collar includes an outer surface forming one or more asymmetrical ridges that selectively restrict translational movement of the collar out of bone relative to into bone.

17. The system of paragraph 16, wherein the collar defines a central axis, and wherein each ridges extends partway around the central axis in a plane orthogonal to the central axis.

18. The system of any of paragraphs 10 to 17, wherein the collar is configured to retain the pin in the bone without threaded engagement between the pin and the collar and without threaded engagement between the collar and the bone.

19. A method of fixing bone, the method comprising, in any order: (A) inserting a pin into a bone; (B) disposing a collar operatively on a section of the pin such that the collar extends more than halfway and less than completely around the section of the pin; and (C) driving the collar into the bone to retain the pin in the bone with the collar.

20. The method of paragraph 19, wherein the step of disposing a collar includes a step of deforming the collar with the pin.

21. The method of paragraph 20, wherein the collar defines a hole and extends incompletely around the hole to form a gap adjoining the hole laterally, and wherein the step of deforming the collar with the pin includes a step of deforming the collar to at least temporarily change a size of the gap.

22. The method of paragraph 21, wherein the step of disposing a collar includes a step of receiving the section of the pin in the hole from the gap.

23. The method of any of paragraphs 19 to 22, further comprising a step of shortening the pin by cutting or breaking the pin.

24. The method of paragraph 23, wherein the step of shortening is performing after the step of driving the collar into the bone.

25. The method of any of paragraphs 19 to 24, wherein the step of disposing a collar includes a step of moving the pin and the collar relative to one another transverse to a long axis of the pin.

26. The method of any of paragraphs 19 to 25, wherein the collar defines a hole, and wherein the step of disposing a collar includes a step of moving the collar and the pin relative to one another parallel to a long axis of the pin while the pin extends through hole.

27. The method of any of paragraphs 19 to 26, wherein the step of driving the collar into the bone includes a step of driving the collar into contact with a wall of a pre-formed bore in the bone.

28. The method of any of paragraphs 19 to 27, wherein the step of driving the collar into the bone causes the pin and the section of the collar to travel into the bone as a unit.

29. The method of any of paragraphs 19 to 28, wherein the step of driving the collar into the bone causes the collar to rotate less than one-half revolution, if any.

30. The method of any of paragraphs 19 to 29, wherein the step of driving the collar into the bone urges the collar into the bone translationally.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A system for bone fixation, comprising:
a pin configured to be inserted into a bone; and
a deformable collar to retain the pin in the bone;
wherein the collar is configured to be operatively disposed on the pin such that the collar extends more than halfway and less than completely around the pin,
wherein the collar defines a through-axis and has an axial dimension measured along the through-axis, wherein the collar includes an inner surface configured to face the pin, wherein the inner surface defines a surface feature that is complementary to each surface feature of a plurality of surface features of the pin, wherein the surface feature of the collar has an axial extent that is less than the axial dimension of the collar, and wherein the collar is configured to be seated on the pin without threaded engagement between the collar and the pin.

2. The system of claim 1, wherein the surface feature of the collar is curved along the through-axis of the collar.

3. The system of claim 1, wherein the collar has a first end opposite a second end and defines a hole extending through the collar from the first end to the second end, wherein the hole is open on one side of the collar from the first end to the second end to form a gap that is contiguous to the hole, and wherein a size of the gap is configured to change as the collar is being operatively disposed on the pin.

4. The system of claim 1, wherein the collar is configured to be operatively disposed on the pin by movement of the pin and the collar relative to one another transverse to a long axis of the pin.

5. The system of claim 1, wherein the pin is formed of metal and the collar is formed of polymer.

6. The system of claim 1, wherein each surface feature of the plurality of surface features of the pin is configured to discourage sliding of the collar along a long axis of the pin after the collar is operatively disposed on the pin at the surface feature of the pin.

7. The system of claim 6, wherein the plurality of surface features of the pin includes a longitudinal array of notches or protrusions defined by the pin, and wherein each notch or protrusion extends at least partway around the long axis of the pin in a plane that is orthogonal to a long axis of the pin.

8. The system of claim 1, wherein the collar is configured to be operatively disposed on the pin at only a finite plurality of discrete, predefined, alternative axial positions defined by the surface features of the pin along a long axis of the pin.

9. The system of claim 1, wherein the collar includes an outer surface forming one or more asymmetrical ridges that selectively restrict translational movement of the collar with respect to the bone.

10. A system for bone fixation, comprising:
a pin configured to be inserted into a bone; and
a deformable collar to retain the pin in the bone;
wherein the collar is configured to be operatively disposed on the pin such that the collar extends more than halfway and less than completely around the pin,
wherein the collar defines a through-axis and has an axial dimension measured along the through-axis, wherein the collar includes an inner surface configured to face the pin, wherein the inner surface defines a surface feature that is complementary to each surface feature of a plurality of surface features of the pin, wherein the surface feature of the collar has an axial extent that is less than the axial dimension of the collar, wherein the pin defines a long axis, and wherein each surface feature of the plurality of pin surface features extends completely and uniformly around the long axis in a respective plane that is orthogonal to the long axis.

11. A method of fixing bone with the system of claim 1, the method comprising, in any order:
inserting the pin of claim 1 into a bone;
disposing the collar of claim 1 operatively on a section of the pin such that the collar extends more than halfway and less than completely around the section of the pin; and
driving the collar into the bone to retain the pin in the bone with the collar.

12. The method of claim 11, wherein the step of disposing the collar includes a step of deforming the collar with the pin.

13. The method of claim 11, further comprising a step of shortening the pin by cutting or breaking the pin.

14. The method of claim 11, wherein the step of disposing the collar includes a step of moving the pin and the collar relative to one another transverse to a long axis of the pin.

15. The method of claim 11, wherein the step of driving the collar into the bone includes a step of driving the collar into contact with a wall of a pre-formed bore in the bone.

16. The method of claim 11, wherein the step of driving the collar into the bone causes the section of the pin and the collar to travel into the bone as a unit.

* * * * *